United States Patent [19]
Berger et al.

[11] Patent Number: 5,665,314
[45] Date of Patent: Sep. 9, 1997

[54] TEMPERATURE CONTROL IN A PORTABLE ANALYTICAL INSTRUMENT

[75] Inventors: Terry A. Berger, Newark, Del.; Mark A. Nickerson, Landenberg, Pa.

[73] Assignee: Hewlett-Packard Company, Palo Alto, Calif.

[21] Appl. No.: 320,486

[22] Filed: Oct. 11, 1994

[51] Int. Cl.⁶ .............................. G01N 30/02; B01D 53/02
[52] U.S. Cl. ............................... 422/89; 422/83; 422/88; 436/161; 95/102; 73/23.41; 73/23.35; 73/863.11; 73/863.12
[58] Field of Search ................ 436/161; 422/83, 422/89, 108, 109, 88; 73/23.41, 23.42, 863.11, 863.12, 23.35; 435/290, 809; 55/386; 95/102

[56] References Cited

U.S. PATENT DOCUMENTS

| | | | |
|---|---|---|---|
| 522,746 | 7/1894 | Uehling | 422/89 |
| 1,016,126 | 1/1912 | Boekel | 435/809 |
| 2,260,111 | 10/1941 | Caldwell | 422/109 |
| 3,229,680 | 1/1966 | Hebert et al. | |
| 3,590,806 | 7/1971 | Locke | |
| 4,351,385 | 9/1982 | Amey | |
| 4,555,232 | 11/1985 | Raccah et al. | |
| 4,911,143 | 3/1990 | Pivot et al. | |
| 4,948,389 | 8/1990 | Klein | 55/20 |
| 5,028,243 | 7/1991 | Rubey | 55/67 |
| 5,282,740 | 2/1994 | Okayasu | |

Primary Examiner—Long V. Le
Attorney, Agent, or Firm—Mark Z. Dudley

[57] ABSTRACT

Sample analysis in a portable analytical instrument, preferably in the form of a gas chromatograph, benefits from temperature control of one or more zones in the instrument by way of thermal energy developed from an energy reservoir. In a preferred embodiment, analytical instrument performs chromatographic analysis and the selected zone comprises a temperature-controlled thermal chamber, or oven (124) which includes a heating unit (118), a temperature sensor (128), and a cooling unit (130). A separation column column (118) is positioned within the oven (124). The energy reservoir comprises a first reservoir (125) of heating fluid in the form of a compressed light hydrocarbon, a second reservoir (126) of a compressed inert gas, or a combination thereof. A controlled temperature in the oven (124) resulting from the operation of the heating unit (118) and/or cooling unit (130) may be effected in response to a control signal generated by a computer (122). A sample mixture passing through the column (118) is thereby exposed to a desired temperature profile according to a selected program so that the sample (111) will separate into its components for subsequent detection by a detector (124).

16 Claims, 4 Drawing Sheets

TEMPERATURE CONTROL IN A PORTABLE ANALYTICAL INSTRUMENT

FIELD OF THE INVENTION

The present invention relates to analytical instruments and, more particularly, to portable analytical instruments including temperature control of one or more zones in the analytical instrument.

BACKGROUND OF THE INVENTION

Modern analytical instruments are particularly susceptible to performance variations due to the temperature of certain devices within the system, or to variations in the ambient temperature conditions in which the analytical instrument is operated. Maintenance of the requisite temperature of one or more devices in the instrument is typically accomplished by electrically-powered heating means, such as an electrical resistance heater. Such means require considerable power and accordingly most conventional analytical instruments are operated in a laboratory setting where adequate electrical power is available.

Prior art attempts to adapt an analytical instrument to field-portable use have not been fully successful due in part to an unresolved need for a lightweight, portable, self-contained, and inexpensive energy source for powering a temperature control system. Arrays of lightweight rechargeable batteries have been attempted, but such arrays are expensive, bulky, and have inadequate storage capacity. Larger storage batteries, such as lead-acid batteries, offer greater storage capacity but are heavy, bulky, and subject to leakage of the electrolyte, which is corrosive. The size, weight, and upkeep of a gasoline-powered generator makes it generally impractical for use in nearly all applications, and especially those wherein the analytical instrument is meant to be highly portable, self-contained, and hand-held. Solar energy conversion devices are not a reliable source of energy if not coupled with ancillary equipment, such as storage batteries, to overcome periods without sunshine, and to handle peak current demands.

Accordingly, a need exists for a portable analytical instrument having at least one zone therein that may be selectively heated and/or cooled by use of a temperature control system operating on a truly compact, lightweight, and inexpensive power source.

SUMMARY OF THE INVENTION

Accordingly, a first preferred embodiment of a system for temperature control of a zone in a portable analytical instrument may be constructed according to the present invention to include a reservoir of heating fluid, said fluid having energy chemically stored therein; a first converter for receiving a flow of the heating fluid and effecting an exothermic thermochemical reaction that converts the energy stored in the heating fluid into heat; a flow regulator, responsive to a first control signal, for controlling the flow of the heating fluid to the converter so as to determine a selectable quantity of heat so generated; and a first heat transport for transporting the quantity of heat from the converter to the zone. A second preferred embodiment of the temperature control system may further include a reservoir of cooling fluid; a second converter for receiving a flow of the cooling fluid and effecting an endothermic reaction that absorbs heat; a flow regulator, responsive to a second control signal, for controlling the flow of the cooling fluid to the converter so as to determine a selectable quantity of heat so absorbed; and a second heat transport for transporting the quantity of heat from the zone to the converter. A temperature sensor, for sensing the temperature of the zone and providing a temperature sense signal, and a computer may be provided, for determining the current temperature of the zone from the sense signal, comparing the current temperature to a desired temperature, and in response, providing the a selected one of said first and second control signals.

The present invention also contemplates the construction of an analytical instrument for receiving and analyzing a sample, wherein the analytical instrument includes the first or second preferred embodiment of the temperature control system for effecting temperature control of a selected zone of the analytical instrument.

In a particularly preferred embodiment, an analytical instrument may be constructed for effecting chromatographic analysis of the sample, and includes a temperature control system as described hereinabove for controlling the temperature of a selected zone of the analytical instrument; a first zone including an injection port for receiving the sample and combining the sample with a mobile phase to create a sample mixture; a second zone including a separation column having a retentive media therein for effecting separation of the sample chemical mixture into at least one component; means for providing a selectable flow of the sample mixture in the separation column; and a third zone including a detector for detecting the component.

DETAILED DESCRIPTION OF THE PREFERRED EMBODIMENTS

The apparatus and methods of the present invention may be employed to effect temperature control of one or more selected zones in a portable analytical instrument. The term "zone" is meant to apply to any of the portions, devices, subsystems, or apparatus that are assembled to form an analytical instrument. The terms "analysis" and "analytical" are meant broadly to include both qualitative and quantitative analytical methods, detection, or observation of physical or chemical parameters. Additionally, the apparatus and methods described herein may be applied to directly or indirectly effect selective temperature control of an element, substance, or material in the form of a "sample" that is present in the selected zone. The term "portable" as applied to an analytical instrument is meant primarily to include a compact, manually-deployable analytical instrument that will find advantageous use outside of the typical laboratory setting. However, the teachings of the present invention may be applied to non-portable and laboratory instruments as well.

Chromatographic analysis of gaseous sample is the preferred mode of analysis according to the practice of the present invention, and the following description of the invention will be directed to a portable gas chromatographic analytical system. However, the teachings herein may be applied to a portable analytical instrument for effecting a chromatographic analysis of liquids, multiple component gases and liquids, and mixtures thereof capable of regulated flow. Moreover, it should be understood that the teachings herein are applicable to instruments that operate using other analytical methods or that analyze or detect other physical parameters and phenomena. Mass spectrometry is one such analytical method.

Figure 1:
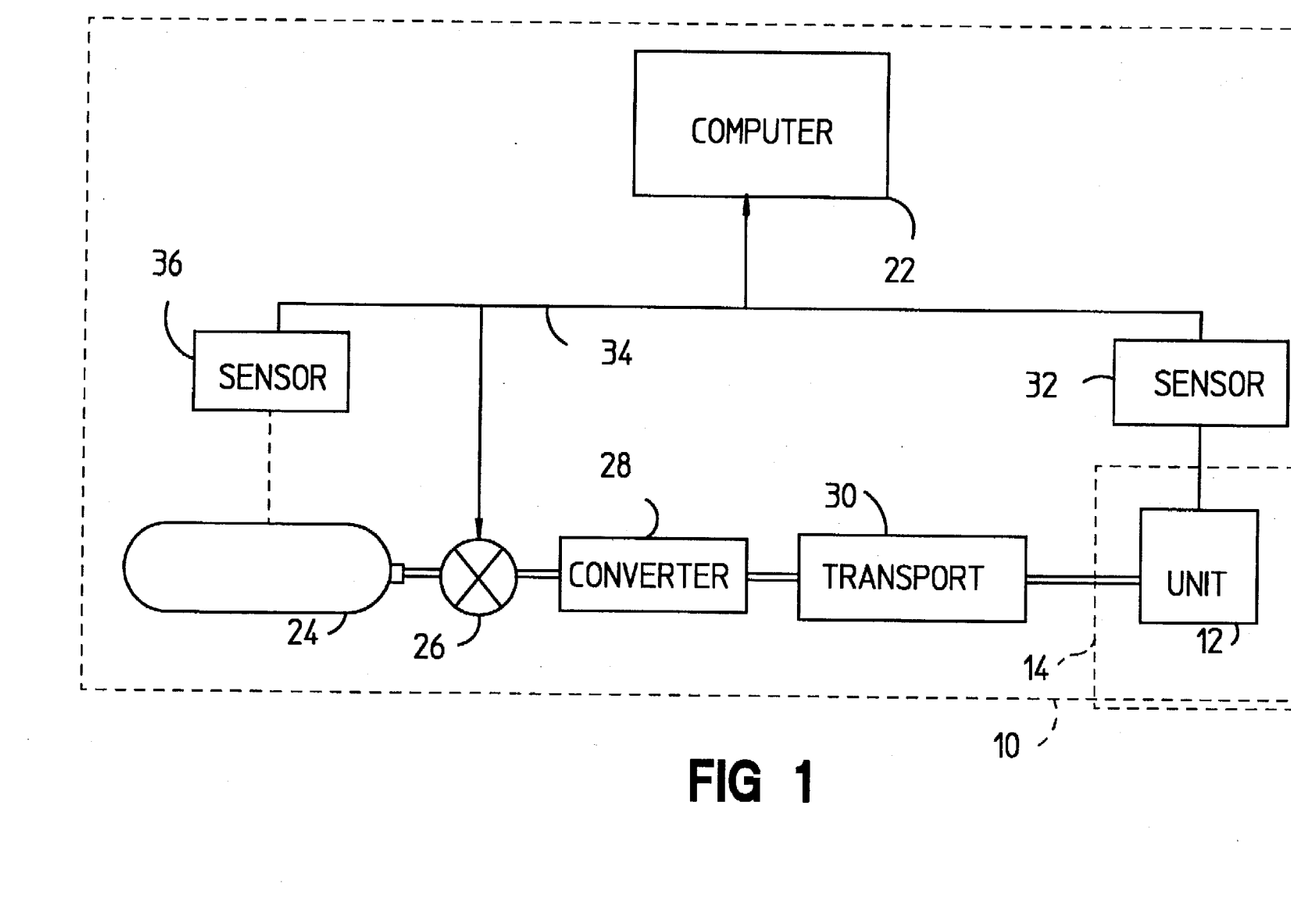
FIGS. 1 and 2 are simplified schematic representations of first and second preferred embodiments of a temperature control system constructed according to the teachings of the present invention for operation in a portable analytical instrument.
Figure 2:
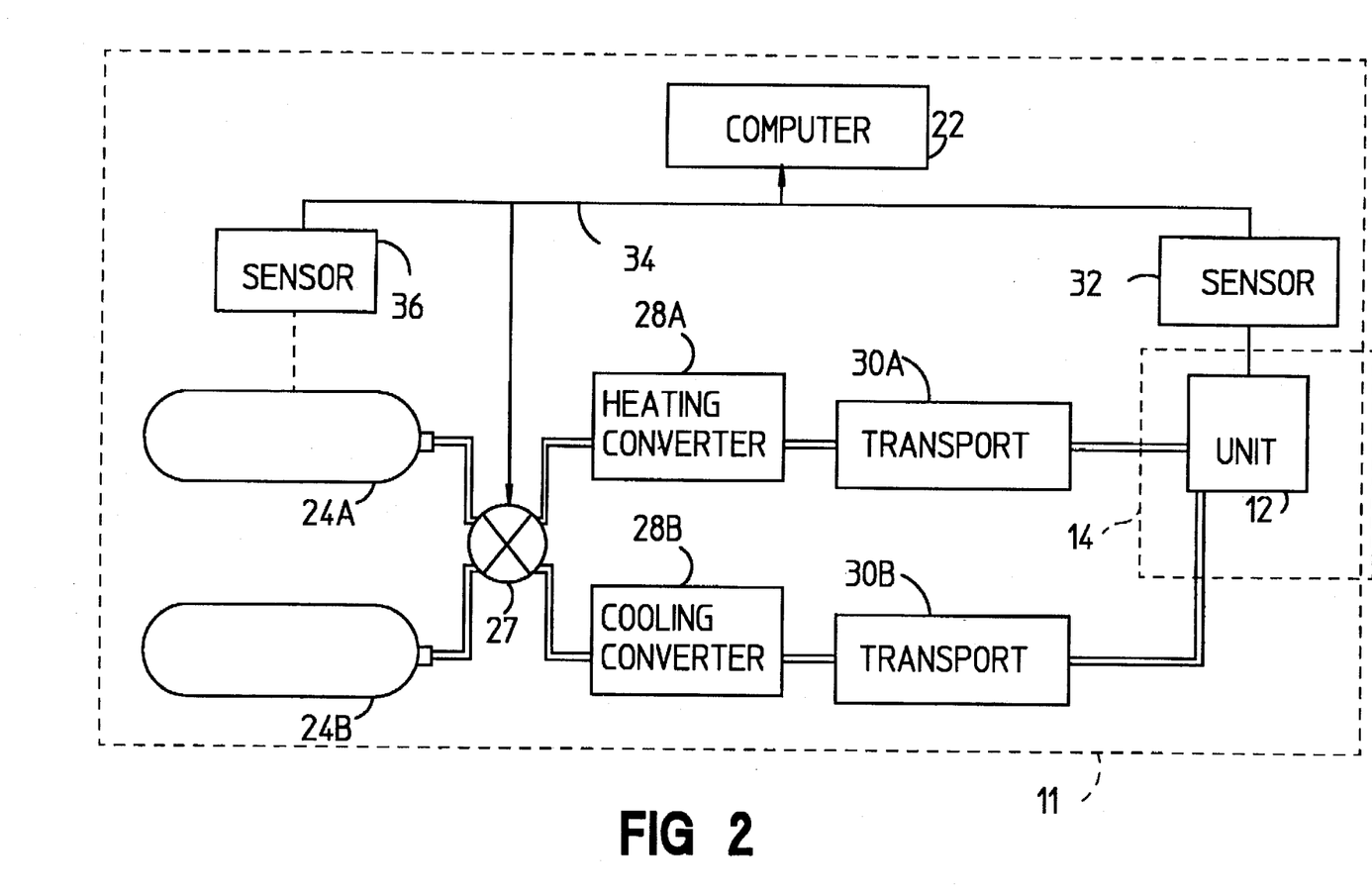

Accordingly, and as illustrated in FIGS. 1 and 2, the present invention is directed to an apparatus and method for temperature control of an analytical instrument 14. In particular, a first preferred temperature control system 10 may be constructed for effecting a selected temperature of a zone 12 situated within an analytical instrument 14. By indication of the overlap between the temperature control system 10 and the analytical instrument 14, FIGS. 1 and 2 illustrate that the system 10 and analytical instrument 14 may be constructed as separate apparatus that are interconnected or otherwise jointly operated at the zone 12. Alternatively, and as will be discussed with respect to FIG. 3, it is contemplated that the system 10 may operate completely within, or be subsumed within, the analytical instrument 14.

Under the control of a computer 22 and a flow regulator 26, a reservoir 24 of heating fluid is made to release a flow of heating fluid to a converter 28. The heating fluid flow, preferably under pressure due to the prior storage of sufficient fluid in the reservoir, enters the converter 28 where it is subject to an exothermic thermochemical reaction, effectively converting the received fluid into a controlled amount of heat and (depending upon the heating fluid) some waste by-products. The heat thus generated is provided from the converter 28 to the zone 12 via a heat transport 30.

The temperature of the zone 12 is sensed by a temperature sensor 32 which provides a temperature sense signal on a data and control signal bus 34 to the computer 22. The temperature sense signal is utilized by the computer 22 to determine the current temperature of the zone 12 and to correct, if necessary, the temperature of the zone 12 by way of a regulator control signal to the flow regulator 26. The data and control signal bus 34 may also carry a reservoir sense signal from an optional reservoir sensor 36. The reservoir sense signal is contemplated as being useful for representing the quality or quantity of the gas held in the reservoir 24. For example, the reservoir sensor 36 may sense the weight or internal pressure of the reservoir 24 so as to represent the amount of energy stored in the reservoir 24, or the reservoir sensor 36 may sense a particular indicator or structural configuration on the exterior of the reservoir 24 representing parameters useful in the conversion process described below such as the type, grade, preferred use, or origin of the heating fluid stored therein.

The heating fluid in the reservoir 24 is selected from known fluids having energy that is chemically-stored therein and available for release in an exothermic thermochemical reaction. The preferred heating fluid may be selected from a group of combustible fuels that are characterized as having: (a) a high energy-to-weight ratio, (b) a capability for storage in a dense (e.g., liquid) state, and (c) a propensity for "clean" combustion (i.e., with little or no waste byproducts). The described group includes the class of liquefied light hydrocarbons, such as a combustible gas (preferably in the form of propane, butane, hydrogen, or methane); liquid hydrocarbons, such as hexane, iso-octane, gasoline, or kerosene; or other liquid fuels, such as alcohol. Accordingly, the converter 28 is operated to effect a controlled combustion of the heating fluid on demand. One preferred mode of combustion includes modulation of a continuous or pulsed flow of the heating fluid by the valve 26. In another preferred mode of controlling the combustion, the combustion mode is contemplated as being controlled or enabled by a process of catalytic conversion of the fuel to heat. Such catalytic process may include the production of heat without a flame, as known in the art of catalytic conversion of fuels to heat. In a still further mode of combustion, especially preferred for combustion of a liquified gas such as propane, the converter 28 is operated to prepare the fuel for combustion by causing expansion or nebulizing of the fuel from its liquid to a gaseous state. The fuel more easily mixes with air, thereby improving the combustion and/or catalytic conversion.

Waste byproducts generated by the preferred liquified gases are typically carbon dioxide and water vapor, which in most applications are not troublesome to vent from the temperature control system 10 into the ambient atmosphere that is outside the instrument 14. Any undesireable waste products may be either allowed to condense for later removal, or are vented to the atmosphere in a way to lessen their offensive nature, such as by adequately diluting the waste output with air.

As illustrated in FIG. 2, a second preferred embodiment of a temperature control system 11 operable with respect to an analytical instrument 14 may be constructed to include a first reservoir 24A of a pressurized heating fluid and a second reservoir 24B of a pressurized cooling fluid. Under the control of the computer 22 upon a multiport flow regulator 27, a heating fluid flow and/or a cooling fluid flow are respectively directed to a heating converter 28A and a cooling converter 28B. The heating fluid flow, still under pressure, enters the heating converter 28A for exothermic conversion into a controlled amount of heat. Heat generated by the heating converter 28A is provided to the zone 12 via a first heat transport 30A. The cooling fluid flow, still under pressure, may be directed to the cooling converter 28B which may be operated in an endothermic reaction so as to absorb heat in a cooling manner. Heat from the zone 12 may be drawn to the cooling converter 28B from the zone 12 by way of a second heat transport 30B.

One benefit of the second preferred embodiment 11 is that in addition to the heating fluid being optimized for the aforementioned conversion to heat in the heating converter 28A, the addition of a cooling fluid allows for controlled cooling of the zone 12. Hence, a preferred heating fluid would include any one of the above-listed light hydrocarbon fuels. A preferred cooling fluid may be selected from the category of inert, pressurized gasses such as air, nitrogen, helium, carbon dioxide, and the like, or liquids such as distilled water. Additionally, the second reservoir 24B may be constructed such that the cooling fluid may be pressurized and thermally insulated to an extent such that the cooling fluid is considered cryogenic.

Figure 3:
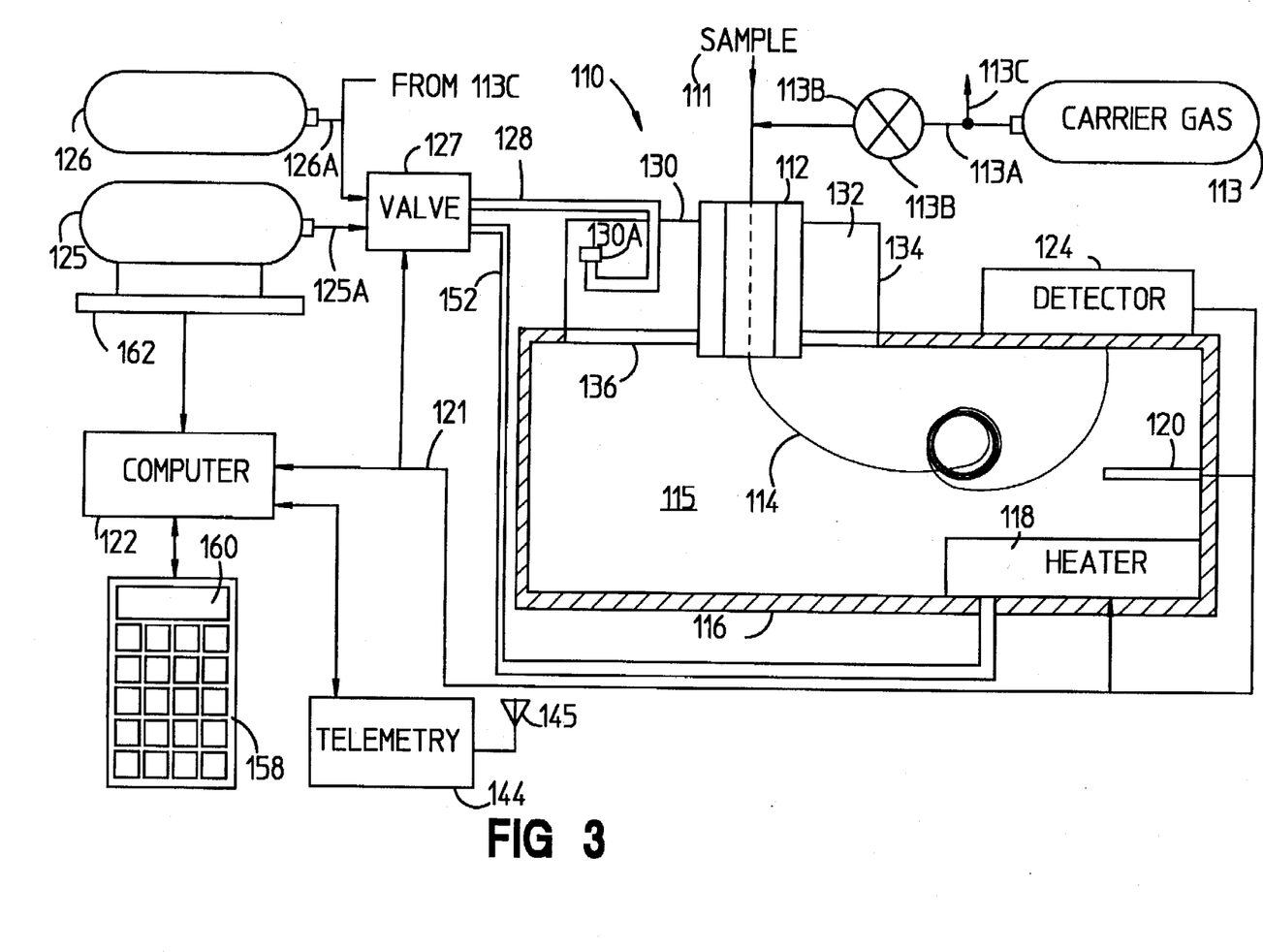
FIG. 3 is a simplified schematic representation of preferred embodiment of a portable analytical instrument in the form of a gas chromatographic analysis system constructed according to the teachings of the present invention.

With reference now to FIG. 3, a preferred embodiment of a portable analytical instrument in the form of a chromatographic analytical system 110 will be understood. The basic mechanism underlying chromatographic analysis is the separation of a sample chemical mixture into individual components by transporting the mixture in a carrier fluid through a specially prepared separation column having a retentive media therein. The carrier fluid is referred to as the mobile phase and the retentive media is referred to as the stationary phase. The principal difference between liquid and gas chromatography is that the mobile phase is either a liquid or a gas, respectively. Liquid chromatography devices are capable of analyzing much heavier compounds than gas chromatography devices. However, gas chromatography detection techniques are more sensitive and therefore are generally preferred. The present invention contemplates the use of either method, although for the purposes of clarity, a gas chromatograph is illustrated.

In a gas chromatographic analysis, an inert carrier gas is passed through a temperature-controlled column which contains a stationary phase in the form of porous sorptive media, or through a hollow capillary tube having an inner diameter in the range of few hundred microns coated with the stationary phase. A sample of the subject mixture is injected into the carrier gas stream and passed through the column. Separation is due primarily to differences in the partial pressures of each sample component in the stationary phase versus the mobile phase. These differences are a function of the temperature within the column. As the basic techniques for the preparation, separation, and detection of sample components are known to those skilled in the art, the description to follow will be directed primarily to the temperature control of one zone of a portable gas chromatograph. The zone may comprise, for example, the portion of the chromatograph occupied by a separation column, inlet, detector, or sample preparation station. The teachings herein comprehend the use of, for example, techniques for subjecting at least a portion of the chromatographic column to a specific temperature profile, and methods of controlling flow of a fluid in a chromatographic analytical system by an electronic pressure control system, as disclosed in Klein, et al., U.S. Pat. Nos. 4,994,096 and 5,108,466, the disclosures of which are incorporated herein by reference.

In particular, the illustrated chromatographic analytical System 110 supports programmed temperature control of an oven in a gas chromatographic analysis such that separation of the sample components is aided by differences in the volatility characteristics of each component. The present invention offers the advantage of high resolution detection of all sample components in a minimized time period, because each component is emerging from the column at its optimum temperature. (As used herein the term resolution refers to the distinctness of graphed peaks generated by known detection apparatus, wherein each peak is representative of the detection of a sample component.) Because the highest temperature may occur at the end of a test, the present invention offers the feature of cooling the zone before beginning the next analysis.

For example, the time required between temperature programmed chromatographic analyses can be reduced by cooling various sections of the chromatographic equipment to bring the temperature in that section down to a desired level prior to beginning the next analysis. In addition it is contemplated that during a chromatographic analysis the illustrated system may be operated to utilize a temperature profile which has a portion below ambient temperature, particularly in the analysis of highly volatile components, or in analysis performed by the chromatographic analysis system 110 while deployed in an adverse (high-temperature) environment. Along these lines, it will be appreciated that the illustrated system provides for selective cooling of at least one zone of the system when necessary.

Accordingly, a preferred embodiment of a portable analytical instrument in the form of a gas chromatograph is shown in FIG. 3 and is generally designated 110. In order to perform a chromatographic separation of a given sample compound, a sample 111 is injected into a fluid, preferably in the form of a pressurized carrier gas, by means of an injection port 112. The carrier gas is supplied to the injection port 112 from a carrier gas reservoir 113 via a first pressure line 113A and a fluid flow controller preferably in the form of a valve 113A. A second pressure line 113C may be provided in certain applications as will be described below. As known to those skilled in the art, the operation of the flow controller serves to control the pressure and/or the volumetric flow rate of the carrier gas in the system 110. The carrier gas may comprise one or more component gasses, e.g., hydrogen, nitrogen, or helium, depending upon the particular chromatographic separation to be performed.

A column 114, a heating unit 118, and a temperature sensor 120 are positioned within the interior 115 of an oven 116. Heating unit 118 provides heat to the oven interior 115 in response to a control signal generated by a computer 122 according to a temperature control profile, and other operating condition parameters, as will be described in greater detail below. In order to ensure that the temperature within the oven is at a desired level, the sensor 120 generates a feedback signal representative of the temperature in the oven 116, which signal is provided to the computer 122 on a data and control signal bus 121. The temperature in the oven 116 may be controlled as an operating condition according to a profile determined and implemented by the computer 122. Control signals provided on the bus 121 to the heating unit 118 control the operation of the heater 118 within the oven 116. As a result, the carrier gas/sample combination passing through column 114 is exposed to the temperature profile determined by the computer 122.

As the carrier gas (containing the sample) exits the column 114, the presence of one or more sample constituent components is detected by a detector 124. The detector 124 can be any detector known in the art, so long as it is capable of determining at least one physicochemical property of the carrier fluid which exits the column 114. Those skilled in the art will appreciate that the term "detector" is meant to include a wide variety of useful chromatographic detectors, such as the flame ionization detector (FID), photoionization detector (PID), nitrogen phosphorous detector (NPD), flame photometric detector (FPD), thermal conductivity detector (TCD), atomic emission detector (AED), electrolytic conductivity detector (ELCD), and electron capture detector (ECD). Mass spectral detectors (MSD) and infrared spectral detectors are also contemplated.

Depending upon the particular choice of detector 124, the preferred embodiments may also include means for providing support gas to the detector. It will be appreciated that the support gas may comprise one or more component gasses depending upon the detector employed. Suitable support gas sources, valves, and transducers, along with related apparatus (not shown), may be employed as known in the art.

A first reservoir 125 provides a heating fluid on a pressure line 125A to a multiport valve 126. In some applications, the temperature profile envisioned to be applied to column 114 in the oven 116 may be chosen to be above ambient temperature and thus the heater 118 is sufficient for effecting the requisite temperature profile. In other applications, a portion of the temperature profile envisioned to be applied to the column 114 may be chosen to be below ambient temperature. If so, the system may be equipped with a second reservoir 126 providing a cooling fluid on a pressure line 126A to the multipod valve 127. Selective control of the multipod valve 127 by the computer 122 may then provide pressurized flow of the cooling fluid on line 128 to a cooling unit 130 preferably in the form of a restrictor 130A. That is, the desired temperatures in the cooling portion of the temperature profile are achieved through the release of the cooling fluid at the cooling unit 130, whereby the cooling fluid makes a rapid transition from the liquid to the gaseous state. (Alternatively, in the instance that the carrier gas being supplied in the carrier gas reservoir 113 is of a type that may be safely vented to the oven or ambient atmosphere, such as helium, carbon dioxide, nitrogen, or air, the second reservoir 126 may be replaced by way of a connection to the second pressure line 113C such that carrier gas may be provided as the cooling fluid to valve 127.)

Selective control of the valve 127 by the computer 122 provides pressurized flow of the heating fluid on a pressurized line 152 to the heating unit 118. The computer 122 controls oven temperature by one or more of the following with respect to the data and control bus 121: (a) transmitting an appropriate signal to valve 127 which alters the flow of fuel to heater 118, thus respectively altering the amount of fuel converted to heat by the heating unit 118; (b) transmitting a control signal to the heating unit 118; and/or (c) transmitting an appropriate signal to valve 127 which alters the disbursement of cooling fluid through tube 128 to restrictor 130.

The flow of cooling fluid through valve 127 is effected in relation to the receipt of a control signal on line 121 from computer 122. For example, the time during which valve 127 remains open in relation to the temperature sensed in oven 116 by sensor 120 is controlled by computer 122. When valve 127 is open, the cooling fluid is passed through a pressurized cooling fluid line 128, to the cooling unit 130, and into the chromatograph 110. As shown in FIG. 2, the cooling fluid is vented into an inlet chamber 132. An inlet cover 134 surrounds opening 136 in oven 116 so that fluid communication is established therebetween. Cooling fluid exiting restrictor 130A will pass into chamber 132, through opening 136, and into oven 116. In particular, and as shown in FIG. 2, the restrictor 130A may be directed so that cooling fluid exiting the restrictor 130A is directed upwards towards the top wall of cover 134. The sudden expansion of cooling gas fluid passing through the restrictor 130A serves to cool the interior 115 of oven 116. As the cooling fluid is dispersed within the chamber 132, the temperature of the column 114 will also be modified in accordance with the overall temperature of the oven 116 such that modifications to the temperature of the column 114 are within the temperature sensed by sensor 120 and thus transmitted to computer 122.

It will be appreciated that in a modification to the cooling unit 130, the portion of the tube 128 within the inlet chamber 132 may be constructed of a thermally-conductive material, such as aluminum, and arranged in a heat-transporting configuration to maximize heat transfer from the oven interior to the fluid carried by the tube 128. Hence, the passage of the cooling fluid through tube 128 may serve to absorb heat from the oven, thus further causing the cooling fluid to rapidly achieve a gaseous state when released either to the interior 115 or, in still another alternative, to the atmosphere outside of the chromatograph 110. For example, the restrictor 130 may be interposed at a fitting where the tube 128 enters the cover 134; the tubing within the inlet chamber 132 would be coiled before connecting to a vent on the exterior of the enclosure (not shown) of the chromatographic analysis system 110, whereby the cooling fluid would be vented to the ambient atmosphere. In a further modification, an internal fan (not shown) may serve to exchange air through the opening 136 between the oven 116 and into the chamber 132 so as to effect convective cooling as the air passes over the coiled portion of tube 128.

It will be recognized that the preferred embodiment 110 contemplates the inclusion of more systems than those described in relation to the present invention. For example, it will be understood that although computer 122 is shown as a single block, it may further comprise a network and bus system (input/output or I/O) controllers, isolation devices, and other related electronic components for performing control, processing, and communication tasks other than those described herein. Such computer 122 preferably includes a central processing unit, input/output and interface devices, a lightweight, low-voltage power source in the form of a battery or the like, and all associated peripheral devices, such as random access memories and read-only memories in which information and programming can be stored and retrieved by known methods. The computer 122 may include a processor selected from computing devices amenable to the practice of this invention, e.g., one or more computing devices such as computers, microprocessors, microcontrollers, switches, logic gates, or any equivalent logic device capable of performing the computations described herein. The programming associated with computer 122 which is utilized in relation to the present invention will include the control of oven temperature and may include other temperature control functions, such as control of the injection port temperature.

The computer 122 preferably is coupled with an information input device 158 preferably in the form of a keyboard, keypad, or similar means for inputting operating condition parameters, system calibration data, and the like. An information output device 160 such as a light emitting diode (LED) array, an alphanumeric or video display, or audio frequency transducer may also be utilized. The computer 122 may further include memory in the form of volatile and non-volatile storage devices in which input and output information, operating condition parameters, system information, and programs can be stored and retrieved. Operating commands, heating and cooling fluid type information, detector response attributes, column temperature programs, and other information necessary to perform a chromatographic analysis may be entered into the computer 122 by way of the input device 158 or retrieved from memory. Messages prompting the user to enter certain information, such as a desired operating parameter e.g., inlet pressure or linear fluid flow in the column, can be generated by the computer and provided on the information output device 160.

Computer 122 also may provide an appropriate signal to a telemetry section 144 and telemetry output terminal 145. The telemetry section 144 may be constructed as known in the art to operate on low voltage power supplied by the computer 122 for transfer (transmitting and/or receiving) information pertinent to the operation of the gas chromatograph. Preferably, the telemetry section 144 includes a radio frequency transmitter or a combined transmitter/receiver in the form of a radio-frequency transceiver, and the output terminal 145 includes an integral antenna (or provides for connecting to an external antenna). Alternatively, and depending upon the application, it is contemplated that the telemetry unit 144 may be provide in the form of an optical transmitter or transceiver operating on, for example, the infrared band, whereupon the output terminal 145 may include a connection to an optical port. Still alternatively, the telemetry unit 144 may be provided in the form of a network data interface for hardwired connection of the system 110 to a phone line, local area network, or other hard-Wired data transfer apparatus.

Such telemetry is intended to complement the portability of the chromatographic analytical system 110. The chromatographic analytical system 110 may be programmed upon its installation at a remote site such that a particular chromatographic separation can be conducted automatically without human intervention on a repeated, periodic basis. Appropriate information may be entered into computer 122 by the user through way of keypad 158. For example, parameters relating to the temperature profile to be provided at the oven 116 and the injection port 112 during the analysis are entered through keyboard 58. The computer 122 operates to store the entered information into memory for later access. Having entered this information, it is a relatively simple operation for computer 22 to generate the desired temperatures for any given moment in time during the analysis in relation to such temperature profile parameters. The system 110 then is controlled to a desired temperature at the requisite time, even if the task is performed some hours, days, or even weeks later.

In accordance with a particular feature of the invention, the output of the detector is considered one such actual operating condition parameter to be sensed such that a value representative of that parameter is then processed by the computer to derive a portion of the telemetry signal transmitted by the telemetry unit 144. Depending upon the character of the detector output signal (whether discrete, continuous, and/or periodic) and the type (analog or digital), a detector output signal from the detector may be provided on the data and control signal bus 121 to an analog to digital (A/D) converter section in the computer 122; digital signals generated by the A/D converter are then supplied to the internal processor. Other digital information, such as a reservoir sense signal received from an appropriate sensor in a reservoir cradle 162, may be received on the bus 121 and passed directly to the processor for processing and inclusion in the telemetry signal transmitted by the telemetry unit 144. For example, the output of the detector 124 or the sense signal outputted by the reservoir sensor 148 may be determined to cross a predetermined threshold, whereupon the computer 122 may operate the telemetry unit 144 to transmit an alarm signal representative of such condition to a telemetry signal receiving and processing station (not shown) located some distance away.

Figure 4:
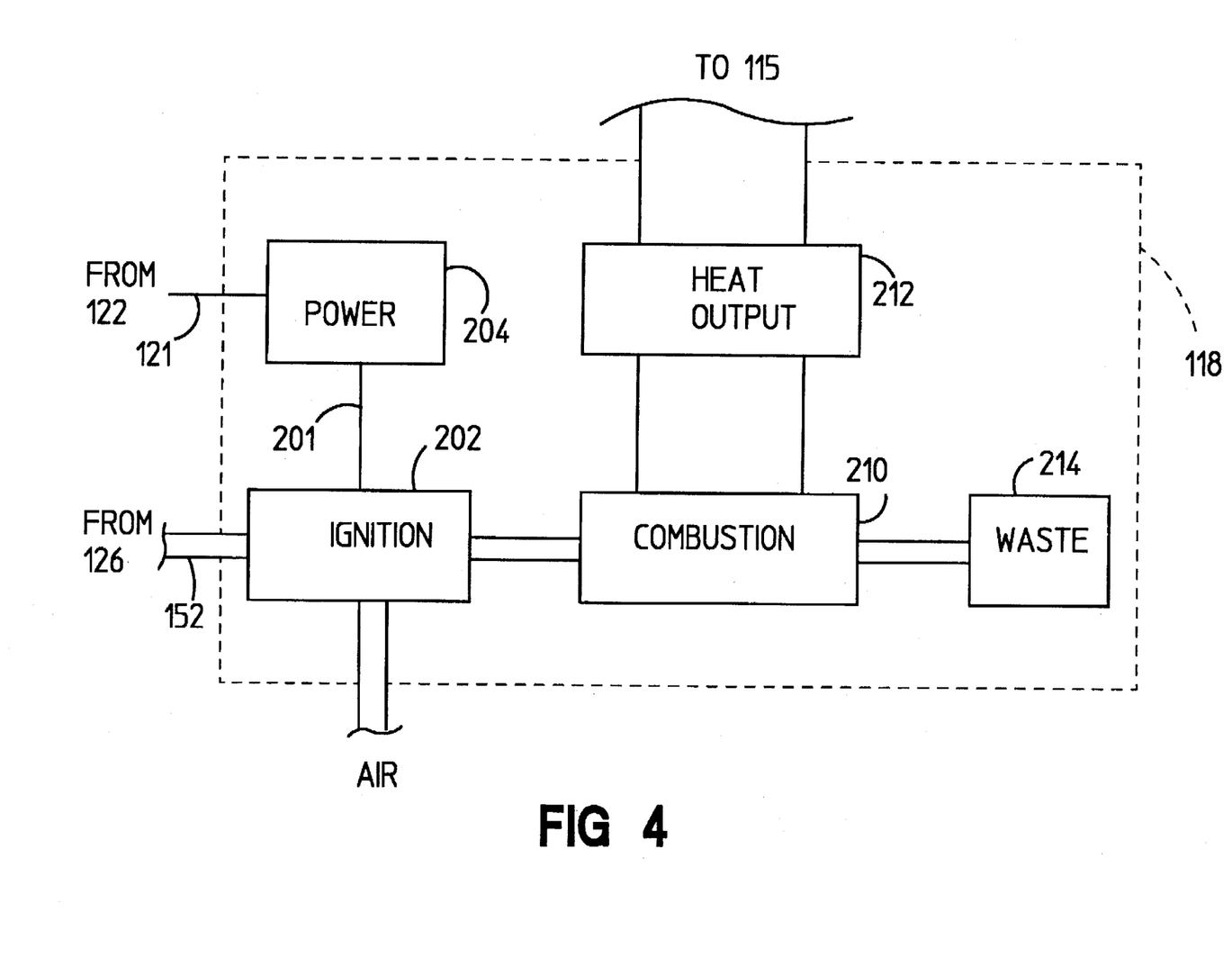
FIG. 4 is a simplified schematic representation of a preferred embodiment of a heating unit operable in the gas chromatographic analysis system of FIG. 3.

Further, the computer 122 may be programmed to effect an analysis in a repeated, periodic fashion, such that the chromatographic analytical system 110 is used only for brief periods. consumption of the heating fluid, cooling fluid, carrier gas, and electrical power is thereby conserved. The telemetry unit 144 may, for example, be kept inactive until needed for effecting periodic communication with a telemetry signal receiving and processing station, or for communication of an unexpected (i.e., alarm) signal FIG. 4 illustrates a preferred embodiment of the heating unit 118. An ignition section 202 receives heating fluid from the heating fluid line 152, ignition control signals on the data and control bus 121 from the computer 122, and ignition power on power line 206 from an ignition power supply section 204. Ambient air and heating fluid are mixed and ignited in the ignition section 202 and the ignited mixture passes to a combustion section 210 (which may follow the ignition section 202, as illustrated, or be integrated with the ignition section 202). The combustion section 210 functions principally to isolate the combustion of the heating fluid from the oven interior 115 (for safety reasons) such that the product of combustion is heat flow to the oven interior 115, directed by way of a heat output means 212, and a flow of combustion by-products, such as waste gasses, condensation, and the like, to a waste section 214. In a particularly preferred embodiment, the combustion section 210 may include a catalytic element for controlled, flameless combustion of the air/heating fluid mixture. The heat output section 212 may comprise passive heat transport devices, e.g., baffles, radiators, plates, fluid-filled pipes, and the like; alternatively, the heat output 212 section may comprise an active heat transport devices, e.g. a fan. The waste section 214 may comprise a channel for venting the waste gasses to the ambient atmosphere outside of the system 110, and a removable container for collection and disposal of condensate. Alternatively, the condensate can be subject to venting/ evaporation to the ambient atmosphere.

Based on the teachings herein, it is contemplated that those skilled in the art may employ known techniques to carry out the particular functions described herein with respect to the sections 202, 204, 210, 212, 214. For example, the ignition power supply may comprise a battery-powered voltage supply that provides a sufficient low-current, high voltage pulse to a spark gap in the ignition section 202; the catalytic element preferred for use in the combustion section may be constructed from known catalytic materials.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A system for temperature control of a zone in a portable analytical instrument, comprising:

a reservoir of heating fluid, said fluid having energy chemically stored therein;

a first converter for receiving a flow of the heating fluid and effecting an exothermic thermochemical reaction that converts the energy stored in the heating fluid into heat, a flow regulator, responsive to a first control signal, for controlling the flow of the heating fluid to the converter so as to determine a selectable quantity of heat so generated;

a first heat transport for transporting the quantity of heat from the converter to the zone;

a reservoir of cooling fluid;

a second converter for receiving a flow of the cooling fluid and effecting an endothermic reaction that absorbs heat;

a flow regulator, responsive to a second control signal, for controlling the flow of the cooling fluid to the converter so as to determine a selectable quantity of heat so absorbed; and a second heat transport for transporting the quantity of heat from the zone to the converter.

2. The temperature control system of claim 1, further comprising:

a temperature sensor for sensing the temperature of the zone and providing a temperature sense signal; and a computer for determining a current temperature of the zone from the sense signal, comparing the current temperature to a desired temperature, and in response, providing a selected one of said first and second control signals.

3. The temperature control system of claim 1, wherein the heating fluid is selected from a group of liquified light hydrocarbons.

4. The temperature control system of claim 3, wherein the group of liquified light hydrocarbons includes propane, methane, butane, and hydrogen.

5. The temperature control system of claim 1, wherein the heating fluid is selected from a group of liquid hydrocarbons.

6. The temperature control system of claim 1, wherein the cooling fluid is selected from a group of inert liquified gasses.

7. The apparatus of claim 1, wherein the cooling fluid comprises a carrier gas.

8. The temperature control system of claim 1, wherein the first converter further comprises an element for catalytic combustion of the heating fluid.

9. An analytical instrument for receiving and analyzing a sample, comprising:

apparatus for receiving and analyzing said sample, said apparatus having therein a plurality of zones, a first zone of said plurality of zones including means for receiving the sample, a second zone of said plurality of zones including means for separating the sample into at least one component, and a third zone of said plurality of zones including means for detecting said component;

a reservoir of heating fluid, said fluid having energy chemically stored therein;

a converter for receiving a flow of the heating fluid and effecting an exothermic thermochemical reaction that converts the energy stored in the heating fluid into heat;

a flow regulator, responsive to a control signal, for controlling the flow of the heating fluid to the converter so as to determine a selectable quantity of heat so generated; and  a heat transport for transporting the quantity of heat from the converter to a selected one of said zones.

10. The analytical instrument of claim 9, further comprising:

a reservoir of cooling fluid;

a second converter for receiving a flow of the cooling fluid and effecting a endothermic reaction that absorbs heat;

a flow regulator, responsive to a second control signal, for controlling the flow of the cooling fluid to the converter so as to determine a selectable quantity of heat so absorbed; and  a second heat transport for transporting the quantity of heat from a selected one of said zones to the converter.

11. The analytical instrument of claim 9, wherein the apparatus for receiving and analyzing said sample is constructed to perform a chromatographic analysis, and wherein:

said receiving means in the first of said zones includes an injection port for receiving the sample and combining the sample with a mobile phase to create a sample mixture;

said separation means in the second of said zones includes a separation column having a retentive media therein for effecting separation of the sample mixture into said component;

means for providing a selectable flow of the sample mixture in the separation column; and  said detection means in the third of said zones includes a detector for detecting the component.

12. The analytical instrument of claim 11, further comprising:

a temperature sensor for sensing a temperature of a selected one of the first, second and third zones and providing a temperature sense signal; and  a computer for determining the temperature of the selected one of the first, second and third zones from the sense signal, comparing the temperature so determined to a desired temperature, and in response, providing the control signal.

13. The analytical instrument of claim 12, further comprising a memory device for storage and retrieval of a program for effecting a desired temperature profile.

14. The analytical instrument of claim 12, further comprising an information input device for receiving information representative of an operating condition.

15. The analytical instrument of claim 12, further comprising an information output device for providing information representative of an operating condition.

16. The analytical instrument of claim 12, further comprising a telemetry section for communication of information representative of an operating condition.

* * * * *